United States Patent [19]

Carver

[11] 4,334,028
[45] Jun. 8, 1982

[54] FLASK

[76] Inventor: Joseph L. Carver, 310 Via Lido Nord, Newport Beach, Calif. 92663

[21] Appl. No.: 222,045

[22] Filed: Jan. 2, 1981

[51] Int. Cl.³ .............................................. C12M 3/00
[52] U.S. Cl. ...................................... 435/284; 215/6; 215/31; 215/228; 220/266; 422/102; 435/285; 435/286; 435/296; 435/299
[58] Field of Search ............... 435/296, 287, 297, 298, 435/299, 300, 301, 284, 285, 286; 422/102; 215/6, 31, 228; 220/265, 266

[56] References Cited

U.S. PATENT DOCUMENTS

| | | | |
|---|---|---|---|
| 824,210 | 6/1906 | Sauer | 215/31 X |
| 1,451,055 | 4/1923 | Sawin | 215/6 |
| 3,449,210 | 6/1969 | Rohde | 435/298 X |
| 3,726,764 | 4/1973 | White | 435/285 |
| 3,732,999 | 5/1973 | Rounkles | 215/6 |
| 3,870,602 | 3/1975 | Froman et al. | 435/296 |

Primary Examiner—Robert J. Warden

[57] ABSTRACT

In a flask suitable for tissue or micro-organism culture, having top and bottom walls, a pair of similar side walls, a closed end wall, a second end wall having an opening therein, a tubular open neck in sealing engaged at one end with the second end wall so as to surround the opening therein, and means for sealing the other end of the neck, the improvement which comprises a frangible zone formed on the top wall for access to the interior of the culture flask.

4 Claims, 3 Drawing Figures

FLASK

BACKGROUND OF THE INVENTION

This invention relates to the field of flasks useful for various types of culture such as micro-organisms, tissues and the like where a means of steril access through the tope side is desirable.

Historically a variety of assemblies have been used for various forms of culture such as tissue, micro-organisms, and the like. Petri dishes have been used for a long time as have culture tubes. In recent years, culture flasks, particularly the type shown in U.S. Pat. No. 3,449,210 to Rohde, have come into wide spread use. These flasks have proven quite useful particularly if diphase mediums are employed. However a problem develops when it is time to remove material such as individual clones, colonies of cells, or organisms which have developed or been in the flask from the flask. At the present time, the types of material used for these flasks are frequently plactics such as polymehtylmethacrylate and polystrene and the top wall of the flas is removed by use of an electric iron. There are two undesirable results which can occur from this procedure. First, the heat form the iron necessary to melt the plastic, although quit localized, does have an effect on the culture. Secondly, the fumes emitted by the melting operation also can effect the culture.

SUMMARY OF THE INVENTION

It is an advantage of the present invention that it provides a way to opent the top wall thereby providing sterile access to the interior of a culture flask without the application of heat or the development of fumes which may adversely affect the culture. It is a further advantage of the present invention that it does not prevent the use of the flask in the normal way for normal tissue culture procedures prior to the opening thereof. This accomplished through the provision of a frangible zone on the top wall of the culture flask.

Other objects and advantages of the present invention will become apparent from the following description.

DETAILED DESCRIPTION

Figure 1:
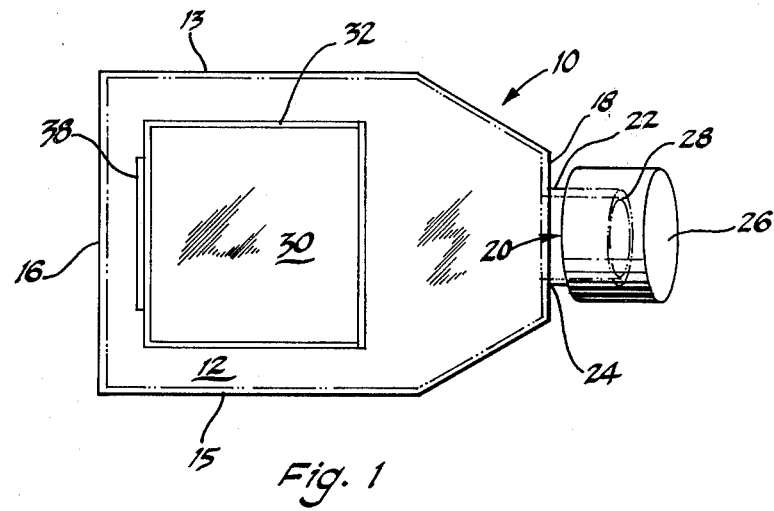
FIG. 1 is a top plan view of a culture flask according to the present invention.
Figure 2:
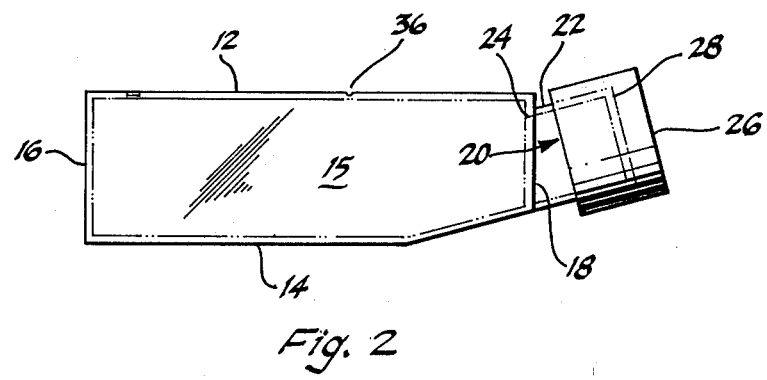
FIG. 2 is a side elevational view of the flask shown in FIG. 1.

As shown with reference to the drawings, wherein like reference numerals are used throughout for corresponding parts, a culture flask is indicated generally at 10. With particular reference to FIGS. 1 and 2, culture flask 10, which may be of any suitable material, such as glass or plastic, which is transparent, relatively rigid, and inert to the culture media, microorganisms, or other materials to be developed and stored therein, is typically a plastic such as polymethylmethacrylate or polystyrene. Culture flask 10 has a top wall 12 and a bottom wall 14 and a pair of similar side walls 13 and 15. A closed end wall 16 is provided as well as a second end wall 18 having an opening 20 therein. A tubular open neck 22 is in sealing engagement at one end 24 with the second end wall 18 so as to surround opening 20 therein. Means, such as cap 26, are provided for sealing the other end 28 of neck 22. The sealing is provided in any conventional manner such as providing coacting threads on neck 22 and cap 26.

A frangible zone 30 is formed in top wall 12 for access to the interior of flask 10. While frangible zone 30 may be formed in a variety of ways, a typical manner of creating frangible zone 30 is by demarking it by means of a linear reduction 32 in the thickness of top wall 12 along which top wall 12 may be cut or broken away through the use of any suitable instrument indicated generally at 34 in FIG. 3. This reduction 32 may be created when the material for top wall 12 is being formed e.g. through a moulding operation or through a milling, cutting, or other thickness reduction mechanism, all as is known in the art.

Figure 3:
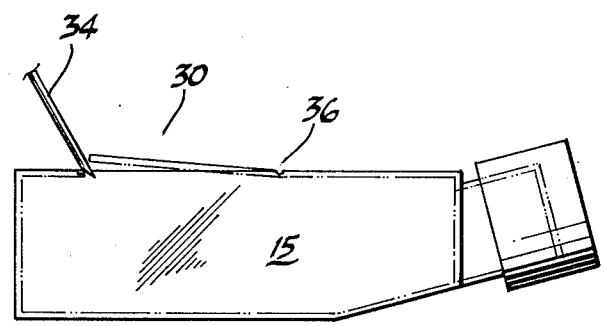
FIG. 3 is a side elevational view of the flask shown in FIG. 1 as the opening operation is in progress.

As shown in FIGS. 2 and 3, one portion 36 of linear reduction 32 may not be reduced in thickness i.e. it may be a greater thickness than the remainder of linear reduction 32. If this is done, when frangible zone 30 is broken away along linear reduction 32, the thicker area 36 will form a hinge for frangible zone 30. Thus frangible zone 30 does not necessarily have to be totally removed but simply bent back out of the way for access into the interior of the flask.

As is shown in the drawings, another portion 38 Of linear reduction 32 may be of greater width than the remainder of linear reduction 32. The wide area 38 creates a suitable place for the insertion of an instrument 34 to commence the breaking away of frangible zone 30 from top wall 12.

While there has been shown and described herein above certain preferred embodiments of the present invention, it would be appreciated that the invention should not be limited thereto but only by the claims.

I claim:

1. In a flask suitable for tissue or micro-organism culture, having top and bottom walls, a pair of similar side walls, a closed end wall, a second end wall having an opening therein, a tubular open neck in sealing engagement at one end with the second end wall so as to surround the opening therein, and means for sealing the other end of the neck, the improvement which comprises a frangible zone integrally formed in the top wall for access to the interior of the culture flask.

2. The culture flask of claim 1 wherein the frangible zone is demarked by a linear reduction in the thickness of the top wall along which the top wall may be cut or broken.

3. The culture flask of claim 2 wherein one portion of the linear reduction in thickness is of greater thickness than the remainder so as to form a hinge for the frangible zone.

4. The culture flask of claim 2 wherein one portion of the linear reduction in thickness is of greater width than the remainder so as to form an area for the initiation of breaking of the frangible zone away from the top wall.

* * * * *